Figure 1:
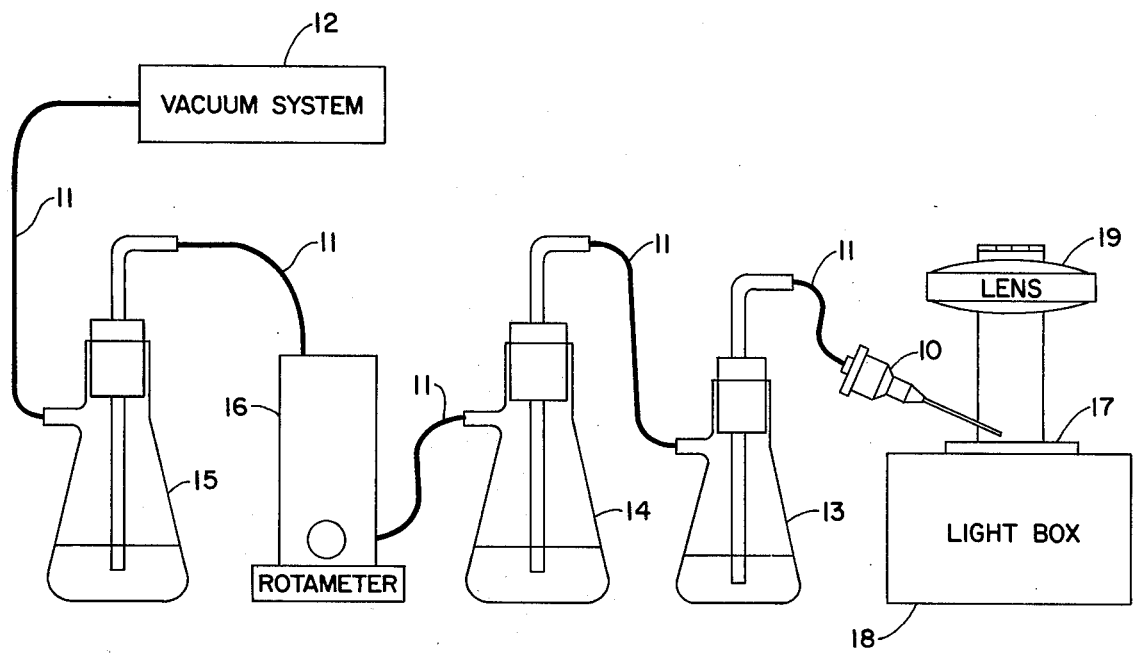

United States Patent [19]

Au et al.

[11] 3,983,007

[45] Sept. 28, 1976

[54] SYSTEM FOR SAMPLING AND MONITORING MICROSCOPIC ORGANISMS AND SUBSTANCES

[75] Inventors: Frederick H. F. Au; Werner F. Beckert, both of Las Vegas, Nev.

[73] Assignee: The United States of America as represented by the United States Energy Research and Development Administration, Washington, D.C.

[22] Filed: Sept. 23, 1975

[21] Appl. No.: 615,962

[52] U.S. Cl. .................. 195/103.7; 195/103.5 R; 195/127; 195/139
[51] Int. Cl.² ......................................... C12K 1/00
[58] Field of Search ................. 195/103.5 R, 103.7, 195/103.5 P

[56] References Cited
UNITED STATES PATENTS 3,028,313   4/1962   Oberdorfer et al. ........... 195/103.5 P

*Primary Examiner*—A. Louis Monacell
*Assistant Examiner*—Robert J. Warden
*Attorney, Agent, or Firm*—Dean E. Carlson; John A. Koch

[57] ABSTRACT

A technique and apparatus used therewith for determining the uptake of plutonium and other contaminants by soil microorganisms which, in turn, gives a measure of the plutonium and/or other contaminants available to the biosphere at that particular time. A measured quantity of uncontaminated spores of a selected mold is added to a moistened sample of the soil to be tested. The mixture is allowed to sit a predetermined number of days under specified temperature conditions. An agar layer is then applied to the top of the sample. After three or more days, when spores of the mold growing in the sample have formed, the spores are collected by a miniature vacuum collection apparatus operated under preselected vacuum conditions, which collect only the spores with essentially no contamination by mycelial fragments or culture medium. After collection, the fungal spores are dried and analyzed for the plutonium and/or other contaminants. The apparatus is also suitable for collection of pollen, small insects, dust and other small particles, material from thin-layer chromatography plates, etc.

4 Claims, 2 Drawing Figures

SYSTEM FOR SAMPLING AND MONITORING MICROSCOPIC ORGANISMS AND SUBSTANCES

The invention described herein was made in the course of, or under, Contract AT(26-1)-539 with the United States Energy Research and Development Administration.

BACKGROUND OF THE INVENTION

This invention relates to sampling and monitoring microscopic organisms and substances, and more particularly to a collection technique and collector apparatus for such sampling and monitoring efforts.

Nuclear power plants will become increasingly important as a source of electrical energy during the next few decades. The potential hazards derived from the use of plutonium in fast-breeder reactors will increase as such facilities are built. It has been estimated that by the year 2000, about 2,700 megacuries of radioactive wastes in the United States will have to be sequestered and about 400 megacuries of transuranic alpha emitters will be part of that waste. Plutonium-239 will be an important constituent of these transuranic alpha emitters and, since its half-life is 24,390 years, it will be a potential hazard for many thousands of years. Therefore, it is important that research be conducted now to determine how environmental and biological factors influence the pathway of plutonium to man.

Plutonium deposited on soil is believed to consist primarily of insoluble particles and of polymers adsorbed on soil particles. Plutonium-containing particles resuspended from soil can enter man by inhalation or ingestion. The larger inhaled particles can be removed from the respiratory system by ciliary action and can then be transferred to the gastrointestinal tract for excretion. The smaller particles may be more dangerous because they can lodge in the pulmonary space where they may be assimilated or retained, thus presenting a continuous source of radiation to the surrounding tissue.

Plutonium originally deposited on soil may be ingested by man by eating contaminated plants or animal products, such as vegetables, meat, and milk. Animals may become contaminated with plutonium through the inhalation of resuspended particles, the ingestion of dust particles deposited on vegetation, the ingestion of soil particles with the food and by grooming, and the ingestion of plants, containing plutonium. The fraction of plutonium that can be assimilated by animals and man is of primary concern; therefore, the chemical nature of the ingested plutonium may be critical. It is probable that the plutonium absorbed by plant roots and translocated to a leaf will be more readily absorbed in the intestines than plutonium deposited on the leaf with resuspended dust.

Plants have been shown to assimilate plutonium from soil. The discrimination factor, defined as the ratio of plutonium disintegrations per minute per gram of dry plant material to the plutonium disintegrations per minute per gram of dry soil, has been reported to be on the order of $10^{-4}$ to $10^{-6}$. Experimental evidence indicated that the rate of plutonium uptake of ladino clover increased with time, resulting in an increase of plutonium incorporation. This increase was explained as possibly being due to the continuing development of the plant roots which increased the number of contact points between the roots and the plutonium particles combined with an increasing biological availability of plutonium. It was suggested that plutonium availability might be enhanced by chelating materials present in the coil.

Another possibility which is supported by experimental results is that soil microorganisms are involved in the transfer of plutonium from soil to plants. It is well known that soil microorganisms are responsible for the solubilization of insoluble mineral soil constituents, thus making them available for plant assimilation. Similar attacks of soil microorganisms on basically insoluble forms of soil-deposited plutonium could convert a certain fraction into a form which is available to plants, animals, and man. Transport studies of selected pollutants, especially actinides and other radionuclides, from growth media to microorganisms and their spores could therefore become an increasingly important technique as a way to determine biological availability of the pollutants by carrying out a few simple experiments. One such technique comprises collecting fungal spores which are then conveniently analyzed for the pollutant. However, most present techniques to collect aerial spores from microorganisms do not exclude contact of the spores with the growth media which results in contamination of the spore surfaces with pollutants from the growth media, leading to erroneous results. A technique which allows convenient spore collection under conditions that strictly exclude any contact with the media contaminated with pollutants would result in great savings in time and money when determining biological availability of such pollutants. Such a technique would especially be useful in the monitoring of pollutants in the vicinity of conventional and nuclear power plants, of nuclear fuel reprocessing facilities, and of metal processing operations.

Thus, in order to carry out the above-mentioned transport studies and to obtain the needed evaluation of the impact of soil microorganisms on the uptake of plutonium and other contaminants by plants, there is a need for more effective methods and apparatus for carrying out the necessary studies, particularly with respect to the determination as to whether soil microorganisms assimilate plutonium and other pollutants and, if so, to quantify the amounts assimilated.

SUMMARY OF THE INVENTION

The present invention is directed to a technique and apparatus for sampling and monitoring microscopic organisms and substances, and particularly for determining the uptake of plutonium and other contaminants by certain soil microorganisms which, in turn, gives a measure of the plutonium and/or other contaminants available to the biosphere at that particular time. Thus, this technique and apparatus provide the above-referenced needed capability to determine in a more simplified and effective manner whether soil microorganisms assimilate plutonium and other contaminants and to quantify the amounts assimilated. The apparatus provides a way of collecting spores without any risk of contamination by mycelial fragments or by contact with the culture medium.

Therefore, it is an object of this invention to provide a collector and collection technique for sampling and monitoring microscopic organisms and substances.

A further object of the invention is to provide a technique and apparatus used therewith for determining the uptake of plutonium and other contaminants by soil microorganisms.

Another object of the invention is to provide an apparatus for collecting spores without risk of contamination by mycelial fragments or by contact with the culture medium.

Another object of the invention is to provide a spore harvesting technique to evaluate the impact of soil microorganisms on the uptake of plutonium and other contaminants by plants.

Another object of the invention is to provide an apparatus suitable for collection of small objects in the 0.1- to 200 μm range, such as aerial spores from certain microorganisms, pollen, small insects, dust and other small particles, material from thin-layer chromatography plates, etc.

Other objects of the invention will become apparent from the following description and accompanying drawings.

BRIEF DESCRIPTION OF THE DRAWINGS

FIG. 1 illustrates an apparatus used in carrying out the technique of the invention; and FIG. 2 is an exploded cross-sectional view of the needle assembly of the FIG. 1 apparatus.

DESCRIPTION OF THE INVENTION

The present invention involves a technique and apparatus used therewith particularly adapted for determining the uptake of plutonium and other contaminants by soil microorganisms, although same can be utilized for sampling and monitoring other microscopic organisms and substances.

The apparatus comprises a small, simple, inexpensive, and versatile device capable of collecting a diversity of small objects in the 0.1- to 200-$\mu m$ range, such as spores from molds and mushrooms, pollen, small particles from air filters, parasites and dust from pelts of animals, samples from thin-layer chromatography plates, etc., whereby the above-referenced transport studies, particularly those involved in plutonium uptake, can be more effectively carried out.

The technique involves adding to a moistened sample of the soil to be tested, a measured quantity of uncontaminated spores of a selected mold; allowing the mixture to sit a predetermined time period under specified temperature conditions; applying an agar layer to the top of the sample; after a period of time wherein spores of the mold growing in the sample have formed, collecting the spores by the apparatus operating under preselected vacuum conditions which permit to collect only the spores with essentially no contamination by mycelial fragments of culture medium; and after collection, drying and analyzing the fungal spores for the plutonium and/or other contaminants.

The vacuum-operated collector apparatus basically consists of a hand-held capsule which contains a filter on a support. One end of the capsule is connected to a small collection tube, and the other end of the capsule is attached to a system capable of creating a partial vacuum. To provide a safety measure to trap any material containing plutonium or other contaminant which might escape during an accidental rupture of the filter, the capsule is connected via tubing to the vacuum or aspiration system via a series of filtering flasks.

To determine whether selected soil microorganisms assimilate plutonium and transfer it to their spores and, if so, to quantify the amounts assimilated and transferred, the collection technique and apparatus of this invention were applied as described hereinafter.

For in vitro studies, *Aspergillus niger* was grown in plutonium-spiked malt agar. This fungus was selected because it is ubiquitous and its properties have been extensively studied. It also produces aerial spores atop a lengthy conidiophore, a feature well suited for spore collection and one which reduces the possibility of cross-contamination with the contaminated nutrient media. Since the plutonium concentration in the spores was expected to be low, it was necessary to use a collection method which provided a sufficiently large biomass to allow quantitation of the plutonium uptake. Also, the collection procedure had to preclude any contamination of the spores with mycelial fragments. For these reasons, as pointed out above, the spore collection methods and apparatus commonly used were not satisfactory. FIG. 1 illustrates a device to meet these requirements which consists of a modified hypodermic needle assembly or collector generally indicated at 10, connected via flexible tubing 11 to an aspiration or vacuum system 12 and which has interposed therebetween a plurality (three in this embodiment) of filtering flasks 13, 14, and 15, with a rotameter or airflow rate controller 16 connected intermediate flasks 14 and 15, filtering flasks 13–15 and rotameter 16 being interconnected by tubing 11. Filtering flasks 13–15 are, for example, each of the 250-milliliter (ml) type containing 50 ml of water and two drops of antifoam agent. The filtering flasks are used as a safety measure to trap any plutonium-containing material which might escape during an accidental rupture of the filter within needle assembly 10. As shown in FIG. 1 and described hereinafter, the needle assembly 10 is used to collect spores from a culture dish 17 positioned on a light box 18 equipped with a magnifying lens 19.

The modified hypodermic needle assembly or collector 10 is illustrated in exploded cross-sectional view in FIG. 2 and comprises an inlet section 20 and an outlet section 21. The inlet section 20 comprises a hollow internally threaded housing or casing member 22 defining a cavity 23 therein, said housing being open at one end and tapering at the opposite end to form a reduced cross-sectional portion 24 having a passage or opening 25 in communication with cavity 23, reduced housing portion 24 being connected to a tube or needle 26 having an internal diameter (I.D.) of about 1 mm, for example, ending in a rounded tip 27. Tube or needle 26 may be connected to housing portion 24 by threads, welding, press fit, or other reasonably gastight connection. Tube or needle 26 may, for example, be of 18-gauge material, 33 mm in length and constructed of metal or plastic. The outlet section 21 of assembly 10 comprises a housing body or member 28 having an externally threaded portion 29 which is threadably engaged with internally threaded housing 22 and is sealed against gas leakage by an O-ring seal 30. Housing body 28 is additionally provided with a centrally located longitudinal passage or opening 31, a flat rim or face 32, and a reduced cross-sectional portion 33 forming a gas outlet to which is connected the flexible tube 11 in FIG. 1. Positioned to abut against the flat rim or face 32 of housing body 28 is a filter support disk 34 which, in turn, rigidly supports a filter 35 having the peripheral edge thereof protected by a ring 36 which abuts against the inner surface of housing member 22 such that disk 34, filter 35, and ring 36 are secured within cavity 23 when the inlet and outlet sections 20 and 21 for assembly 10 are threadably secured together. For example, filter support disk 34 may be constructed of a felt metal material, easily permeable to air, having a 25-mm diameter; filter 35 may constitute a membrane of material such as polyesters or cellulose derivatives; and ring 36 may be constructed of plastic having a 22-mm internal diameter, with the housing members 22 and 28 being constructed of metal or rigid plastic.

It is pointed out that bending of inlet tube 26 at an angle which does not severely restrict airflow facilitates collection of small objects, especially from areas which are otherwise not readily accessible. Also, the internal diameter of cavity 23 may be varied from about 10 to 50 mm. In addition, the support disk 34 may be permanently attached to flat rim or face 32 of housing body 28 by means of welding or a suitable adhesive. However, replacement of disk 34 by a mesh wire screen is not suitable because the small particles impacting on the filter 35 may penetrate the filter and pass through the screen resulting in loss of the sample. In addition, the filter strongly adheres to a mesh wire screen backing even at low airflow rates, resulting in frequent partial or total loss of the sample when trying to remove the filter from the mesh wire screen backing.

Figure 2:
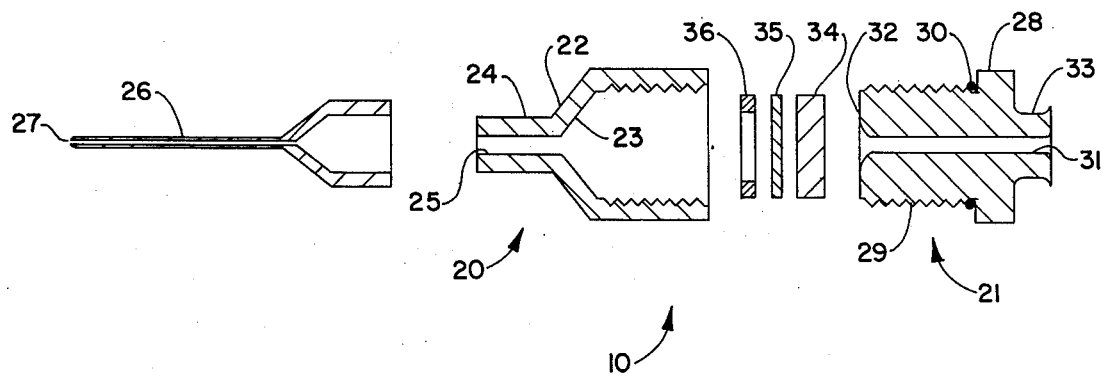

In operation of the apparatus illustrated in FIGS. 1 and 2, the gas outlet 33 is connected via flexible tubing 11 to the controlled vacuum or aspiration system 12 so that an airflow is created through the modified hypodermic needle assembly 10, entering at the tip 27 of tube 26, passing through the filter 35 and the filter support disk 34, and exiting through the gas outlet 33. Small objects are collected by gently touching them with the tip 27, thereby lifting them from their support; the air carries the objects through the tube 26 and impacts them on the surface of filter 35. Controlled airflow is achieved by rotameter 16 or by flow-limiting orifices or other means.

When contamination due to loss of the sample is not a concern, the filtering flasks 13-15 may be omitted. In cases where no vacuum system is available, a rubber bulb can be attached to gas outlet 33 or to flexible tubing 11 to create a partial vacuum such as commonly used for pipetting in laboratories. Even sucking by mouth at flexible tubing 11 is sufficient. Thus, the collection assembly becomes a small, lightweight, portable system especially suited for field use.

Variation of the airflow, by rotameter 16 or other means, allows nondestructive collection of low-density and somewhat sensitive objects such as small insects, as well as high-density particles such as metal powders. It is advantageous to electrically ground any metal parts of the assembly 10 during collection to avoid electrostatic accumulation of particles at the inside walls of the inlet section 20. It is also advantageous to slightly tap the assembly 10 after collection, while held in an upright position and with air still flowing through the assembly, to transfer all particles which might have accumulated at the inside of the inlet section 20 onto the filter 35. The physical mass of the material accumulating on the filter 35 can be conveniently regulated by varying the duration of collection.

With the above-described apparatus, spores can be collected without any risk of contamination by mycelial fragments or by contact with the culture medium. Additional advantages of this collection assembly are its simplicity, low cost, ease of handling, and its capacity to collect relatively large amounts of material in a short time.

The harvesting of plutonium-contaminated spores of *Aspergillus niger*, as above-referenced, using the inventive technique involves placing the culture dish 17 on light box 18 equipped with magnifying lens 19. The spores were detached by gently touching them with the tip 27 of the hypodermic needle assembly 10 and were impacted onto the filter 35. An airflow rate of 1.6 lmp (liters per minute) was used to vacuum up the spores after microscopic examination had shown that no conidiophores were deposited on the filter at this flow rate. However, at airflow rates exceeding 2 lpm, substantial portions of the conidiophores accumulated with the spores. A two-minute collection period was found to be optimal for massing the spores on the filter. Longer collection times resulted in an excessive accumulation of spores on the inner surface of the holder. An electric timer was used to control the lengths of collection periods; it was connected to the light box which was preset to terminate illumination after 2 minutes. Based on five two-minute collection periods per plate, the average spore recovery was estimated to be 95-98 percent.

In a set of experiments, malt agar (25 g agar plus 30 g malt extract per liter) was buffered to pH 2.5 with 0.1 M monopotassium phthalate and 0.1 M hydrochloric acid. Plutonium-238 nitrate in 4 N nitric acid was added to aliquots of the buffered agar to obtain plutonium concentrations of 112, 224, and 448 pCi/ml. Twenty-ml aliquots of the spiked medium were pipetted into petri dishes to make three sets of four dishes with 2.24, 4.48, and 8.96 nCi per dish, respectively, containing 1.34 g of dry mass each. The dishes were inoculated with 0.3 ml of *Aspergillus niger* spore suspension per dish ($10^8$ spores per ml), placed in plastic bags, and incubated for 33 days at 25° ± 1°C. The aerial spores were then collected using the collection assembly and technique described earlier, acid digested, and the plutonium activity determined by alpha spectrometry. In separate experiments, the moisture content of the spores was determined by placing them in desiccators over $P_2O_5$ immediately after collection. The total weight loss amounted to only 2-3 percent.

Following collection of the spores, the agar with the mycelium from each dish was transferred to a glass beaker and melted on a hot water bath. The mycelial mat was carefully removed with a spatulum, placed on a Buchner funnel fitted with a No. 2 Whatman filter, and washed three times with 50-ml volumes of distilled water. The mat was over-dried at 60°C, acid digested, and the plutonium activity determined by alpha spectrometry.

In an additional experiment, an attempt was made to remove any soluble plutonium which might have migrated from the culture medium via the conidiophore surfaces to the spore surfaces. The plutonium-containing spores were treated for 5 minutes with an aqueous solution containing 0.85 percent NaCl, 0.1 percent $Na_2$ EDTA, and 0.1 percent of a 2 percent Tween 80 surfactant solution. The filtrate and the spores were then analyzed for plutonium. No activity could be detected in the filtrate, whereas the spores showed the activity expected.

The described set of experiments was designed to determine the relationship between the plutonium concentrations in the culture media (agar) and the amount of plutonium translocated to the mycelia and spores. In these experiments, plutonium was added to the agar as a nitrate. To prevent hydrolysis of the plutonium nitrate and the formation of a colloid (which may start at a pH > 2.8), the pH of the agar medium was kept at pH 2.5 by the addition of a buffer. The specific activity of the mycelia isolated in these experiments was found to be a linear function of the plutonium concentration in the agar. The total amount of plutonium in the mycelium was about 25 percent of the amount added to the agar; the percentage absorbed was independent of the plutonium concentration originally present in the agar. It should be noted that in this set of experiments, the conditions were optimized for maximum plutonium uptake; i.e., a soluble form of plutonium was evenly distributed throughout the media under conditions which prevented plutonium hydrolization and polymerization.

The specific activity of the spores was more than two orders of magnitude less than the specific activity of the mycelia grown on agar. About 0.05 percent of the plutonium was translocated to the spores. This indicates a translocation barrier between the mycelia and the spores. A nearly linear relationship was found to exist between the activity found in the spores and the activity added to the agar media.

As a means to compare the uptake of plutonium by plants grown on plutonium-contaminated soil, the discrimination factor defined earlier is commonly used. Because the soil water content may fluctuate within wide limits, the discrimination factor is based on dry soil weight. When trying to apply the same concept to plutonium uptake of *Aspergillus niger* grown on culture media, it must be kept in mind that the soil used in plant growth serves a dual function: (1) it is a mechanical support to the plants, and (2) it is a source of nutrients. In culture media, such as agar, broth, or hydroponic solutions, water is an integral part of the mechanical support for the substrate and is thus comparable to soil. Consequently, a discrimination ratio could be based on the wet weight of the culture medium. Values calculated on this basis are several orders of magnitude higher than the discrimination factors found for plant uptake from soil. This may indicate a lower discrimination against plutonium absorption and translocation in the fungus, or a greater availability of plutonium in the agar system. However, it should be kept in mind that soil/plant and culture medium/fungus systems are entirely different. Plants assimilate only minor amounts of inorganic solids from the soil, that means mass transfer of solids is very small; therefore, for practical purposes, no soil depletion occurs during one growth season. Plants synthesize their organic materials, whereas microorganisms depend solely on the culture medium for their inorganic and organic materials. This results in a significant transfer of solids from the culture medium to the microorganism. The material balance, including water, is constant for such a system, except for small losses due to microbial metabolism. On the other hand, higher plant obtain all of their carbon from the atmosphere, and their metabolism, ion absorption, and translocation systems are vastly different to those found in fungi.

The percentage of plutonium transferred from the culture media to the microorganisms could be used as another basis of comparison, but this approach gives little, if any, information about concentration or discrimination effects. As a solution to understanding plutonium transport, a "transport factor" (TF) is introduced which is applicable to culture media where the distribution of nutrients and pollutants is uniform. This factor TF, which is concentration-independent, is defined as that fraction of the total plutonium that is transported from the media to the tissue, divided by the fraction of the total dry mass transported from the media to the tissue, or $$TF = \frac{Pu_T/Pu_M}{M_T/M_M}$$

Where:
$Pu_T$ = total plutonium content of tissue (e.g., mycelium, spores)
$Pu_M$ = total plutonium originally present in the parent medium
$M_T$ = dry mass of tissue
$M_M$ = dry mass originally present in the parent medium The transport factor is identical to the ratio of the specific activities (mycelium/agar, etc.), or to the familiar discrimination factor when based on the dry mass of the culture medium. It immediately shows if accumulation of or discrimination against the pollutant has occurred. TF > 1 indicates an accumulation; TF < 1 defines discrimination against the pollutant.

The transport factors defining the movement of plutonium from substrate to mycelia and on to the spores have been established but are not deemed necessary for inclusion herein to understand the invention. These values show that under the experimental conditions employed, an accumulation (TF > 1) of plutonium occurred in the mycelium of *Aspergillus niger*. All transport factors based on agar media were essentially concentration-independent. On the other hand, the transport factors for plutonium from mycelia to spores are generally smaller by more than two orders of magnitude (TF < 1). This demonstrates that discrimination occurred against plutonium transport from mycelia to spores (mycelial dry mass and mycelial plutonium concentration values used in these calculations were those determined after spore collections).

The implications of these findings are threefold. First, it is well known that soil microorganisms play an important role in plant nutrition, chemically transforming substances that are unavailable to plants to forms available for plant uptake. This suggests that soil microorganisms may also be able to attack deposited plutonium, making it more available to plants. Thus, years of microbial activity combined with plant root development would result in an increase of the plutonium uptake rate by plants with time. This would explain the experimental results which showed an increase in the plutonium uptake rate by plants, such as clover, with time, particularly when considering that the rhizosphere is the region of intensive and extensive microbial activity. Consequently, once plutonium enters the soil, the importance of plant assimilation as a pathway to man will increase with time, and it may be that in several decades, plutonium uptake by plants may likely increase to a higher level than is currently believed.

Second, an additional impact of fungal uptake of plutonium may be imposed if plutonium is assimilated by fungi and deposited in their spores. Many soil fungi release their spores into the air. If inhaled by man and retained in the respiratory system, this will cause a prolonged radiation exposure of the surrounding tissue in the same manner as resuspended plutonium particles.

Third, the direct uptake of plutonium from soil by animals and man could also be affected by soil microbial activity. As pointed out in the introduction, the plutonium particles presently associated with dust and soil that can be inhaled and ingested by animals and man are generally insoluble. If, over the years, soil microorganisms change part of this plutonium into forms more biologically available to man and animals, then inhalation and ingestion of plutonium-containing soil particles will present an increasing hazard to man.

It has thus been shown that the present invention provides a collector and collection technique for sampling and monitoring microscopic organisms and substances, which is particularly useful for determining the uptake of contaminants, such as plutonium, by soil microorganisms which, in turn, gives a measure of the contaminant available to the biosphere at that particular time. Applying the apparatus and technique of this invention to the uptake of plutonium, the following operational sequence is utilized:

1. A measured quantity of uncontaminated spores of a selected mold is added to a sample of the soil to be tested, which had been preferably moistened to 50–60% of its moisture holding capacity although the moisture range can vary from 10–80%;
2. This mixture is allowed to sit 10 to 30 days under specified temperature conditions;
3. An agar layer is then applied to the top of the sample;
4. Allowing 3 to 33 days for spores of the mold growing in the sample to form;
5. Collecting the spores by the vacuum collection apparatus under preselected vacuum conditions which collect only the spores with essentially no contamination by mycelial fragments or culture medium;
6. Analyzing the dried fungal spores for their plutonium content.

The above-described apparatus and technique or method was developed and is presently being used mainly to collect aerial spores of mold species grown on culture media contaminated with actinides and metals such as uranium, plutonium, americium, mercury, lead, arsenic, and cadmium. This method has already provided valuable data on plutonium and americium transport from contaminated soil and on transport of a spectrum of radionuclides from uranium mill tailings to microorganisms. Aerial spores from suitable molds grown on spiked nutrient media and collected with this new system also show a potential as convenient radionuclide standards and calibration sources. Especially when using combinations of radionuclides, certain problem areas and uncertainties such as arising from chemical changes possibly occurring during storage of liquid standards or from solvent evaporation might be eliminated by using radionuclides incorporated into spores. Another distinct advantage of using spores is their ready digestability as compared to soil and vegetable or animaal tissue samples.

Transfer of many other kinds of pollutants to microorganisms and their spores, including pesticides and their degradation products, as well as nutrients can be studied by using this method. By modifying the tip 27 and applying a high airflow rate (up to 1,500 ml/min.) even other aerial portions of certain molds could be picked off for separate analysis to determine pollutant concentrations in the molds. In other experiments, pollen from plant species was conveniently collected with this device using either a vacuum system, a rubber bulb, or suction by mouth. This technique could prove valuable for plant research and plant breeding. Particles from particular spots as small as 1–2 $mm^2$ on air filters or thin-layer chromatography plants were quantitatively removed with the device and spread out onto the filter. Small insects such as aphids or parasites from animal pelts can also be collected. The filters containing the collected objects can be examined directly under a microscope, which makes this method especially valuable for screening purposes.

While a particular embodiment of the apparatus and specific materials, temperatures, pressures, etc., and operation steps have been described or illustrated, modifications will become apparent to those skilled in the art, and it is intended to cover in the appended claims all such modifications as come within the spirit and scope of this invention.

What is claimed is:

1. A method for determining the uptake of contaminants from soils by selected soil microorganisms comprising the steps of: mixing the soil sample to be tested which has been moistened to 10–80% of its moisture holding capacity with a measured quantity of uncontaminated spores of a mold featuring aerial spores, maintaining this mixture of soil and mold spores at specified temperature conditions for a specified time period, applying an agar layer to the top of the thus treated soil sample, allowing a time period for the mold growing in the sample to form aerial spores, collecting the thus formed aerial spores, and drying and analyzing the spores for the contaminants.

2. The method defined in claim 1, wherein the step of collecting the formed aerial spores is carried out by contacting the spores with a vacuum apparatus wherein the spores are drawn thereinto and collected on a filter permeable to the passage of air therethrough.

3. The method defined in claim 2, wherein the step of collecting the formed aerial spores by the vacuum apparatus includes adjustably controlling the airflow through the apparatus so as not to exceed 2 liters per minute.

4. The method defined in claim 1, wherein the step of maintaining the mixture of soil sample and mold spores was carried out at room temperature for a time period of 3 to 33 days.

* * * * *